(12) United States Patent
Clerc et al.

(10) Patent No.: US 10,278,841 B2
(45) Date of Patent: May 7, 2019

(54) DUODENAL METABOLIC STENT

(71) Applicant: Boston Scientific Scimed, Inc., Maple Grove, MN (US)

(72) Inventors: Claude O. Clerc, Marlborough, MA (US); Kurt Geitz, Sudbury, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 236 days.

(21) Appl. No.: 14/084,073

(22) Filed: Nov. 19, 2013

(65) Prior Publication Data

US 2014/0081416 A1 Mar. 20, 2014

Related U.S. Application Data

(63) Continuation of application No. 13/088,671, filed on Apr. 18, 2011, now abandoned.

(60) Provisional application No. 61/330,050, filed on Apr. 30, 2010.

(51) Int. Cl.
*A61F 2/90* (2013.01)
*A61F 5/00* (2006.01)
*A61F 2/848* (2013.01)
*A61F 2/04* (2013.01)
*A61F 2/82* (2013.01)

(52) U.S. Cl.
CPC ............ *A61F 2/90* (2013.01); *A61F 5/0076* (2013.01); *A61F 2/848* (2013.01); *A61F 2002/045* (2013.01); *A61F 2002/828* (2013.01); *A61F 2220/005* (2013.01); *A61F 2220/0016* (2013.01); *A61F 2220/0058* (2013.01); *A61F 2250/0039* (2013.01)

(58) Field of Classification Search
CPC ............... A61F 2/852; A61F 2002/828; A61F 2002/045; A61F 5/0076; A61F 5/0079; A61F 2/90

See application file for complete search history.

(56) References Cited

U.S. PATENT DOCUMENTS

| | | | |
|---|---|---|---|
| 5,306,300 A | * | 4/1994 | Berry .......................... 623/23.64 |
| 5,575,818 A | * | 11/1996 | Pinchuk .................... A61F 2/90 |
| | | | 606/195 |
| 5,679,470 A | | 10/1997 | Mayer |

(Continued)

FOREIGN PATENT DOCUMENTS

WO 2008/098255 8/2008

*Primary Examiner* — Andrew M Iwamaye
(74) *Attorney, Agent, or Firm* — Seager, Tufte & Wickhem, LLP

(57) ABSTRACT

In at least one embodiment, the invention is directed to an endoluminal device comprising a stent and a sleeve. In one embodiment, the endoluminal device is implanted in a portion of the gastrointestinal tract. In some embodiments, the stent has a first region and a second region where the first and second regions provide different levels of radial force. In one embodiment, the first region is made from a plurality of first wires having a first diameter and the second region is made from a plurality of second wires having a second diameter which is smaller than the first diameter. In other embodiments, the endoluminal device has at least one engagement mechanism engaging the stent to the sleeve, the endoluminal device to a body lumen, and any combination thereof. In at least one embodiment, the endoluminal device has a wall with at least one opening therein.

19 Claims, 8 Drawing Sheets

(56) References Cited

U.S. PATENT DOCUMENTS

| | | | |
|---|---|---|---|
| 5,759,192 A | 6/1998 | Saunders | |
| 5,769,884 A * | 6/1998 | Solovay | A61F 2/07 606/194 |
| 5,824,077 A | 10/1998 | Mayer | |
| 6,325,822 B1 | 12/2001 | Chouinard et al. | |
| 6,340,367 B1 | 1/2002 | Stinson et al. | |
| 6,398,807 B1 | 6/2002 | Chouinard et al. | |
| 6,527,802 B1 | 3/2003 | Mayer | |
| 6,585,758 B1 | 7/2003 | Chouinard et al. | |
| 6,622,604 B1 | 9/2003 | Chouinard et al. | |
| 6,673,102 B1 * | 1/2004 | Vonesh | A61F 2/07 623/1.11 |
| 6,685,738 B2 | 2/2004 | Chouinard et al. | |
| 6,740,121 B2 | 5/2004 | Geitz | |
| 6,755,869 B2 | 6/2004 | Geitz | |
| 6,942,693 B2 | 9/2005 | Chouinard et al. | |
| 7,004,967 B2 | 2/2006 | Chouinard et al. | |
| 7,101,392 B2 | 9/2006 | Heath | |
| 7,122,058 B2 * | 10/2006 | Levine et al. | 623/23.65 |
| 7,160,319 B2 | 1/2007 | Chouinard et al. | |
| 7,435,254 B2 | 10/2008 | Chouinard et al. | |
| 7,438,712 B2 | 10/2008 | Chouinard | |
| 7,594,928 B2 | 9/2009 | Headley, Jr. et al. | |
| 7,670,367 B1 | 3/2010 | Chouinard et al. | |
| 7,771,466 B2 | 8/2010 | Chouinard et al. | |
| 7,938,853 B2 | 5/2011 | Chouinard et al. | |
| 2002/0007210 A1 | 1/2002 | Chouinard et al. | |
| 2003/0040804 A1 * | 2/2003 | Stack et al. | 623/23.7 |
| 2003/0069646 A1 * | 4/2003 | Stinson | 623/23.7 |
| 2003/0135265 A1 | 7/2003 | Stinson | |
| 2003/0149473 A1 | 8/2003 | Chouinard et al. | |
| 2004/0073300 A1 | 4/2004 | Chouinard et al. | |
| 2004/0098095 A1 | 5/2004 | Burnside et al. | |
| 2004/0098099 A1 * | 5/2004 | McCullagh | A61F 2/90 623/1.15 |
| 2004/0158312 A1 | 8/2004 | Chouinard et al. | |
| 2004/0167606 A1 * | 8/2004 | Chouinard | A61F 2/07 623/1.13 |
| 2005/0052644 A1 | 3/2005 | Lewis et al. | |
| 2005/0125075 A1 | 6/2005 | Meade et al. | |
| 2006/0036311 A1 * | 2/2006 | Nakayama | A61F 2/90 623/1.15 |
| 2006/0259113 A1 * | 11/2006 | Nissl | A61F 2/04 623/1.3 |
| 2007/0106370 A1 | 5/2007 | Chouinard et al. | |
| 2007/0179590 A1 | 8/2007 | Lu | |
| 2007/0282453 A1 * | 12/2007 | Weitzner | A61F 2/04 623/23.7 |
| 2008/0178459 A1 * | 7/2008 | Barr | A61F 2/91 29/557 |
| 2008/0221671 A1 | 9/2008 | Chouinard et al. | |
| 2009/0149939 A1 * | 6/2009 | Godlewski | A61F 2/07 623/1.13 |
| 2009/0171442 A1 * | 7/2009 | Young | A61F 2/06 623/1.15 |
| 2009/0254172 A1 * | 10/2009 | Grewe | A61F 2/856 623/1.15 |
| 2010/0016940 A1 | 1/2010 | Mehrdad | |
| 2010/0121461 A1 * | 5/2010 | Sobrino-Serrano et al. | 623/23.68 |
| 2010/0256775 A1 * | 10/2010 | Belhe et al. | 623/23.65 |
| 2010/0274346 A1 | 10/2010 | Chouinard et al. | |
| 2011/0087146 A1 * | 4/2011 | Ryan et al. | 604/8 |

* cited by examiner

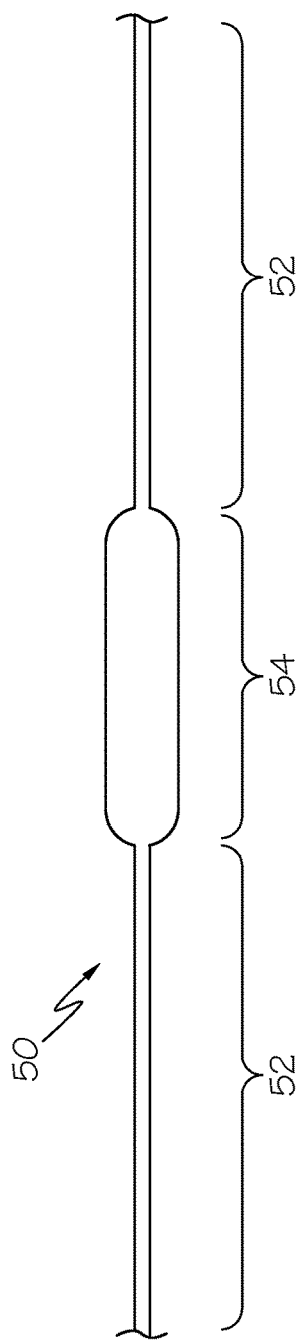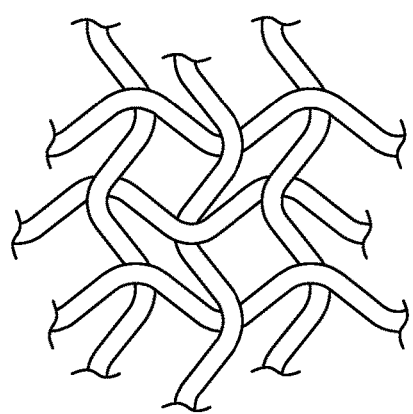

DUODENAL METABOLIC STENT

CROSS-REFERENCE TO RELATED APPLICATIONS

This application is a continuation of application Ser. No. 13/088,671 filed Apr. 18, 2011, which is a non-provisional of Application No. 61/330,050, filed Apr. 30, 2010, each incorporated by reference in its entirety.

STATEMENT REGARDING FEDERALLY SPONSORED RESEARCH

Not Applicable

BACKGROUND OF THE INVENTION

Expandable devices such as stents or other expandable frameworks may be implanted in a variety of body lumens or vessels such as within the vascular system, urinary tracts, gastrointestinal tracts, bile ducts, fallopian tubes, coronary vessels, secondary vessels, etc. Some expandable devices are implanted in a portion of the patient's gastrointestinal tract to treat obesity and medical conditions associated with obesity. Estimates of the incidence of morbid obesity are approximately 2% of the U.S. population and 0.5% worldwide. Recent investigations suggest that the causes of obesity involve a complex interplay of genetic, environmental, psycho-behavioral, endocrine, metabolic, cultural, and socioeconomic factors. Medical conditions associated with obesity include coronary artery disease, hypertension, type II diabetes mellitus, gallstones, nonalcoholic steatohepatitis, pulmonary hypertension, and sleep apnea.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. § 1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to an endoluminal device comprising a stent and a sleeve. In some embodiments, the endoluminal device further comprises an anchor. In one embodiment, the endoluminal device is implanted in a portion of the gastrointestinal tract. In some embodiments, the stent has a first region and a second region where the first and second regions have different levels of radial force. In one embodiment, the first region is made from a plurality of first wires having a first diameter and the second region is made from a plurality of second wires having a second diameter which is smaller than the first diameter. In other embodiments, the endoluminal device has at least one engagement mechanism engaging the stent to the sleeve, the endoluminal device to a body lumen, and any combination thereof. In at least one embodiment, the endoluminal device has a wall with at least one opening therein.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 5 is a schematic view of a wire having sections of different diameters which can be used to form a stent of the endoluminal device of FIG. 2.

FIG. 6 is a schematic view of wires having a plurality of undulations which have been interwoven.

DETAILED DESCRIPTION OF THE INVENTION

Figure 1:
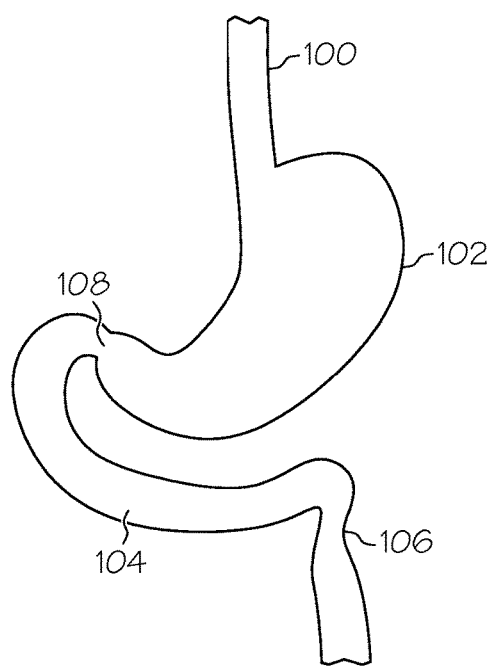
FIG. 1 is a schematic view of a portion of the human gastrointestinal tract.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
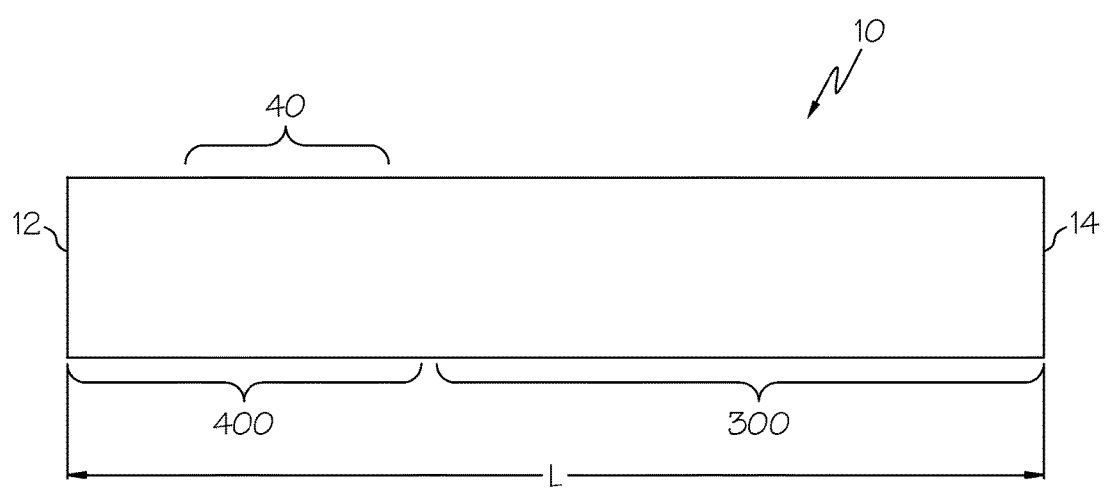
FIG. 2 is a schematic view of an endoluminal device.

An endoluminal device 10 is shown schematically in FIG. 2. In at least one embodiment, the endoluminal device 10 is deployed in a portion of the gastrointestinal tract. FIG. 1 illustrates a portion of the human gastrointestinal tract, including the distal segment of the esophagus 100, the stomach 102, and the small intestine which includes the duodenum 104 (proximate segment of the small intestine), and the jejunum 106. The pyloric part of the stomach leads to the duodenum 104 by way of the gastric outlet or pylorus 108. The pylorus 108 forms the distal aperture of the stomach 102 and has an enclosing circular layer of muscle which is normally contracted to close the aperture but which relaxes to provide an open but restricted passage. The antrum region of the stomach 102 is adjacent to the pyloric part of the stomach. In some embodiments, the endoluminal device 10 is a duodenal metabolic device.

The endoluminal device 10 has a longitudinal length (L) between the proximal end 12 and the distal end 14 of about 30 cm to about 90 cm. The endoluminal device 10 comprises an anchoring portion 400 and a sleeve portion 300. The anchoring portion 400 has a longitudinal length of about 2 cm to about 6 cm. The sleeve portion 300 has a longitudinal length of about 24 cm to about 88 cm. As used in this application, the endoluminal device 10, and portions comprising the endoluminal device 10 discussed below, e.g. the stent 20, the sleeve 30, and the anchor 40, have an expanded state when it is deployed in a body lumen.

In at least one embodiment, the endoluminal device 10 has an anchoring portion 400. At least one of the anchoring portions 400 stabilizes the position of the endoluminal device 10 in the body lumen. As shown in FIG. 2, the anchoring portion 400 forms the proximal region of the endoluminal device 10. In at least one embodiment, the anchoring portion 400 has a longitudinal length of about 2 cm to about 6 cm and a diameter in the expanded state of about 30 mm to about 50 mm. In at least one embodiment, the anchoring portion 40 has a radial force that is substantially greater than the radial force of the sleeve portion 300. In some embodiments, the radial force of the anchoring portion 400 is about 10 to about 1,000 times greater than the radial force of the sleeve portion 300. In this application, the term "radial force" refers to the amount of outward pressure exerted on a body lumen by the region when the endoluminal device is deployed in the body lumen. The radial force is defined as the hoop force HF. The hoop force can be described by the following equation, $HF=P \times 1 \times D/2$, where P is the pressure exerted by the stent, D is the actual diameter of the stent and 1 is the length of the stent section. For braided stents, the radial force increases with increasing number of wires, increasing wire diameter, and increasing braid angle (a).

In at least one embodiment, the anchoring portion 400 comprises at least one anchor 40. In one embodiment, the endoluminal device 10 has one anchor 40, a stent 20, and at least one sleeve 30. In some embodiments, the anchor 40 is an expandable device. In one embodiment, the anchor 40 is a stent. In at least one embodiment, the anchor 40 is laser cut. In one embodiment, the endoluminal device has an anchor stent 40, a stent 20, and at least one sleeve 30. It is within the scope of the invention for any stent to be used as an anchor stent 40. In some embodiments, the anchor stent 40 is a balloon expandable stent. In other embodiments, the anchor stent 40 is a self-expanding stent. In at least one embodiment, the anchor 40 has a variable diameter. In some embodiments, the anchor 40 has a proximal end that is positioned at the proximal end of the endoluminal device 10. In other embodiments, the anchor 40 is positioned a distance away from the proximal end of the endoluminal device 10, as shown for example, in FIG. 2. In this embodiment, the proximal end of the anchor 40 is distal to the proximal end of the endoluminal device 10.

In at least one embodiment, at least a portion of the stent 20 forms the anchoring portion 400 of the endoluminal device 10. In some embodiments, only a portion of the stent 20 is the anchoring portion 400. In one embodiment, the endoluminal device 10 has a stent 20, at least one sleeve 30 and no anchor 40. In other embodiments, the entire stent 20 is the anchoring portion 400. In this embodiment, the endoluminal device 10 has a stent 20 and at least one sleeve 30.

Figure 3:
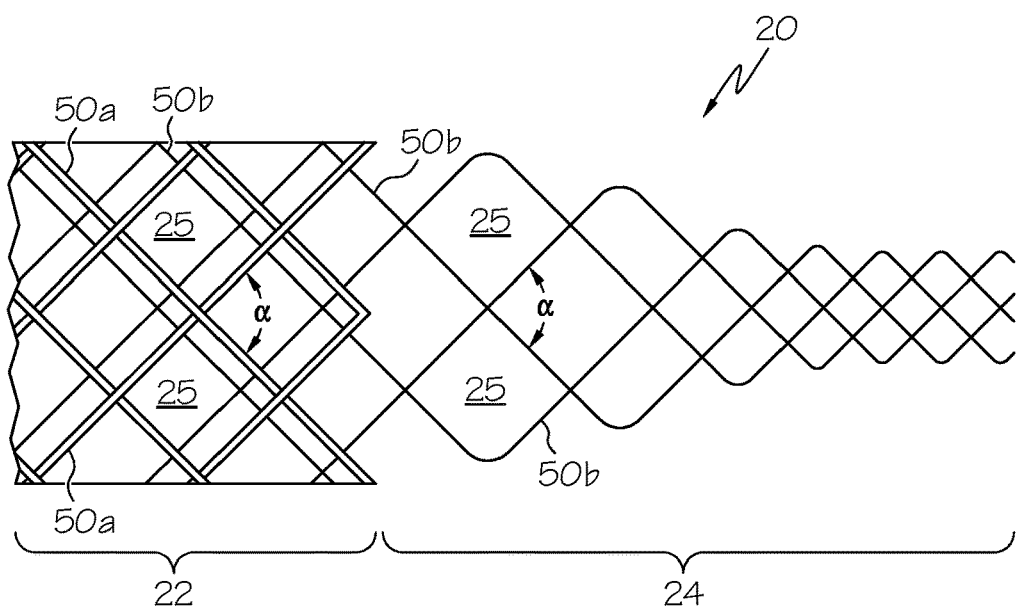
FIG. 3 is a schematic view of a stent forming a part of the endoluminal device of FIG. 2.

In at least one embodiment, the stent 20 and the anchor 40 are each made of a biocompatible non-degradable material. As is known in the art, some stents have a plurality of cells or openings along the length and circumference of the stent. These cells or openings are defined by a plurality of structural members. Structural members of a stent depend upon the construction of the stent and include for example, struts, connectors, and wires. FIG. 3 shows openings 25 that are defined by wires 50 forming the stent 20. In some embodiments, the stent 20 has a retrieval loop (not shown). In other embodiments, the anchor 40 has a retrieval loop (not shown). The retrieval loop is a means by which the endoluminal device 10, or a portion or portions thereof, can be repositioned or removed from the body lumen after implantation. Non-limiting examples of suitable materials for the stent 20 and the anchor 40 are provided below. It is within the scope of the invention for the stent 20 to be self-expandable, balloon expandable, or both balloon expandable and self-expandable.

Although some particular methods of making a stent 20 of the endoluminal device 10 are described in greater detail below, the stent 20 may be made by any method. It is also within the scope of the invention for the anchor stent 40 to be made by any method. For example, the stent(s) 20, 40 may be created by methods including cutting or etching a design from a tubular stock, from a flat sheet which is cut or etched and which is subsequently rolled, or from one or more interwoven wires. In at least one embodiment, the stent 20, 40 is a laser cut stent. Examples of techniques for laser cutting tubular bodies to form stents 20, anchors, or other structures are described in U.S. Pat. No. 5,759,192, the entire contents of which is incorporated herein by reference. As used in this application, the term "interwoven" includes braiding, knotting, knitting, weaving, and combinations thereof. An example of a knotted stent is shown for example in FIGS. 5A-C of U.S. Pat. No. 7,594,928, the entire contents of which are incorporated herein by reference. Any other suitable technique which is known in the art or which is subsequently developed may also be used to manufacture the stent(s) 20, 40 of the endoluminal device 10.

In at least one embodiment, the stent 20 and the at least one sleeve 30 are coextensive along the entire longitudinal length of the endoluminal device 10. In this embodiment, the length of the stent 20 and the length of the sleeve 30 are the same length and equal to the length of the endoluminal device 10. In one embodiment, the stent 20 is disposed within the sleeve 30. In another embodiment, the stent 20 is disposed about the sleeve 30. When the sleeve 30 is disposed within or about the stent 20, the sleeve 30 covers the openings 25 of the stent 20 so that there are no openings in the wall of the endoluminal device 10. In some embodiments, the sleeve 30 forms at least a portion of the entire outer surface of the endoluminal device 10. In other embodiments, the sleeve 30 forms at least a portion of the entire inner surface of the endoluminal device 10. In still other embodiments, the stent 20 is sandwiched between a first sleeve 30a and a second sleeve 30b (not shown). In at least one embodiment, sleeve 30 is a liner.

In at least one embodiment, the stent 20 and the at least one sleeve 30 are coextensive for only a portion of the longitudinal length of the endoluminal device 10. In this embodiment, the stent 20 has a longitudinal length less than the longitudinal length of the sleeve 30. In some embodiments, the stent 20 and the sleeve 30 form the proximal end 12 of the endoluminal device 10 and the sleeve 30 forms the distal end 14 of the endoluminal device 10. In other embodiments, the stent 20 forms the proximal end 12 of the endoluminal device 10 and the sleeve 30 forms the distal end 14 of the endoluminal device 10. In at least one embodiment, the outer surface of the sleeve 30 is attached to the inner surface of the stent 20.

Figure 4:
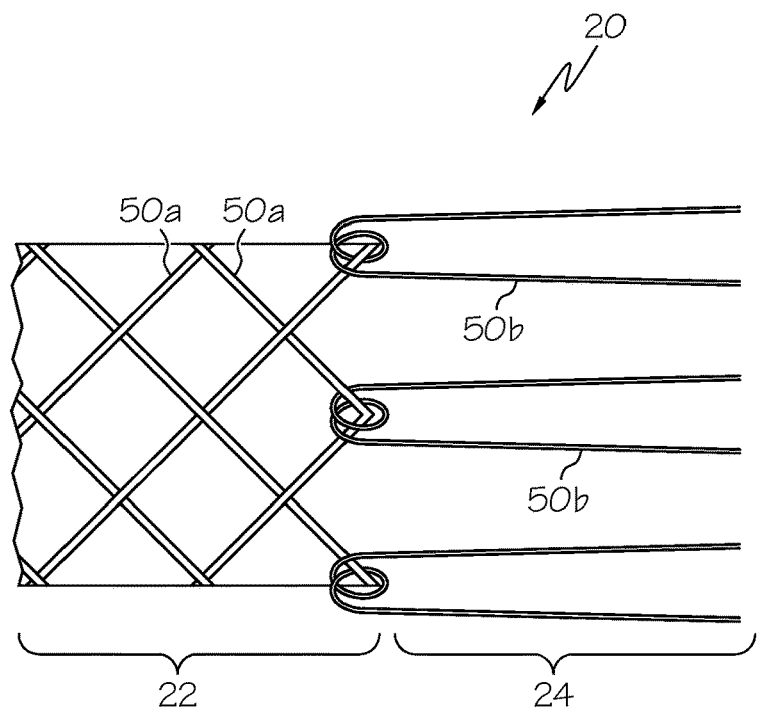
FIG. 4 is a view of a portion of a stent forming a part of the endoluminal device of FIG. 2.
Figure 7:
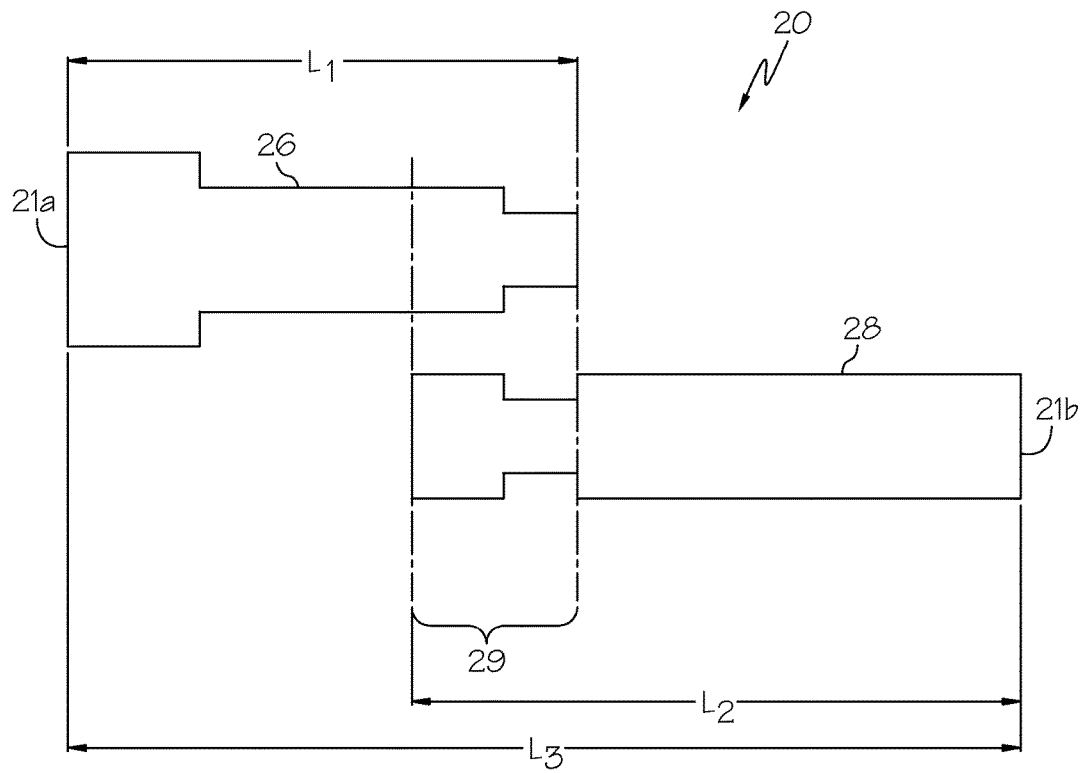
FIG. 7 is a schematic view of a stent forming a part of the endoluminal device of FIG. 2.

In at least one embodiment, the stent 20 has a first end 21a, a second end 21b, a first region 22, and a second region 24. Examples of a stent 20 are shown in FIGS. 3-4 and 7-8. FIGS. 3 and 4 show a schematic example of a stent 20 with first and second regions 22, 24. As shown, the first and second regions 22, 24 are immediately adjacent one another and there are no regions between the first and second regions 22, 24. The first region 22 of the stent 20 has a length of about 20 mm to about 60 mm and a diameter in the expanded state of about 20 mm to about 60 mm. The second region 24 of the stent 20 has a length of about 300 mm to about 900 mm and a diameter in the expanded state of about 15 mm to about 25 mm. In some embodiments, the first region 22 of the stent 20 is the anchoring portion 400 of the endoluminal device 10.

In at least one embodiment, the first region 22 of the stent 20 has a greater radial force than the second region 24 of the stent 20. In some embodiments, the lower radial force of the second region 24 of the stent 20 allows for peristaltic motion when the endoluminal device 10 is deployed in the body lumen. In other embodiments, the lower radial force of the second region 24 of the stent 20 prevents blockage of the bile duct when the endoluminal device 10 is implanted in the gastrointestinal tract. In one embodiment, the second region 24 of the stent 20 is positioned at, or adjacent to, the bile duct.

In at least one embodiment, the stent 20 is formed of a plurality of wires 50 that have been interwoven. In some embodiments, the wires 50 that are interwoven to form the stent 20 are straight. In other embodiments, the wires 50 that are interwoven to form the stent 20 have a plurality of undulations. In one embodiment, wires with a plurality of undulations cover more surface area than wires that are straight. A schematic wires with undulations that have been interwoven is shown for example in FIG. 6. In some embodiments, the plurality of wires defines a plurality of openings 25. In one embodiment, the openings 25 defined by adjacent wires 50a in the first region 22 have a larger area than the openings 25 defined by adjacent wires 50b in the second region 24. In some embodiments, the density of the wires in the first region 22 of the stent is less than the density of the wires in the second region 24 of the stent 20.

In at least one embodiment, the plurality of wires 50 includes a plurality of first wires 50a and a plurality of second wires 50b. The number of first wires 50a can be less than, equal to, or greater than, the number of second wires 50b. In some embodiments, the number of first wires 50 is about 20 wires to about 72 wires. In at least one embodiment, the first wires 50a have a first diameter and the second wires 50b have a second diameter which is less than the first diameter. In some embodiments, the first diameter is substantially the same along the length of the first wire 50a and the second diameter is substantially the same along the length of the second wire 50b. In at least one embodiment, the wires 50a that have the first diameter have a greater radial force than the wires 50b that have the second diameter.

In at least one embodiment, the first and second wires 50a, 50b form the first region 22 of the stent 20 and only the second wires 50b form the second region 24 of the stent 20, as shown for example in FIG. 3. The first wires 50a form a first braid and the plurality of second wires 50b is interwoven into the braid formed by the first wires 50a. As shown, the second wires 50b are interwoven into the first braid so that each second wire 50b is parallel to a first wire 50a. The second wires 50b extend beyond the first region 22 to form the second region 24 of the stent 20. In some embodiments, the second wires 50b form a braid. In other embodiments, the second wires 50b forming the second portion 24 are intertwined with one another so that portions of one second wire 50b are wrapped about portions of another second wire 50b to form a knotted stent portion. As mentioned above, an example of a knotted stent is shown for example in FIGS. 5A-C of U.S. Pat. No. 7,594,928.

In at least one embodiment, a stent 20 having a plurality of first wires 50a and second wires 50b which are braided to form a first and second region 22, 24 of the stent 20, as shown in FIG. 3, can be made by first braiding the first wires 50a to form a first braided stent portion and then incorporating the second wires 50b into the first braided stent portion. As shown in FIG. 3, the second wires 50b are interwoven into the first braid so that each second wire 50b is parallel to a first wire 50a. The second wires 50b can be incorporated into the braid of first wires 50a by any method and secured to the braided first wires 50a by any method. In one embodiment, the second wires 50b are incorporated into the braid of first wires 50a by hand. Because the second wires 50b are a part of both the first and second regions 22, 24 of the stent 20, the second wires 50b have a greater length than the first wires 50a.

In other embodiments, the first region 22 of the stent 20 is made of a plurality of first wires 50a interwoven to form a first braid and the second region 24 is made of a plurality of second wires 50b interwoven to form a second braid and the first and second regions 22, 24 are engaged to one another to form the stent. This is shown schematically in FIG. 4. The first and second regions 22, 24 of the stent 20 are engaged to one another by any suitable means. As shown in FIG. 4, the second region 24 is engaged to the first region 22 by looping a portion of a second wire 50b about one of the first wires 50a. In some embodiments, each first wire 50a has a first diameter along the length of the wire 50 and each second wires 50b has a second diameter along the length of the wire 50.

In at least one embodiment, the braid angles α of the wires 50 forming the first and second regions 22, 24 of the stent 20 are matched so that the stent can be compressed for delivery to a body lumen. Thus, the braid angle α in the first region 22 is the same as the braid angle α of the second region 24 of the stent 20.

In at least one embodiment, the wire 50 has at least one first section 52 with a first diameter and a second section 54 with a second diameter greater than the first diameter. In some embodiments, the first diameter is about 0.0005 inches to about 0.006 inches and the second diameter is about 0.008 inches to about 0.020 inches. In one embodiment, the first diameter is 0.005 and the second diameter is 0.012. In at least one embodiment, the first diameter is substantially the same along the length of the first section 52 of the wire 50 and the second diameter is substantially the same along the length of the second section 54 of the wire 50. In at least one embodiment, the wire 50 at least one first section 52 with a first diameter and a second section 54 with a second diameter is made by partial drawing, chemical or electrochemical etching, centerless grinding, or any other technology.

In at least one embodiment, the first section 52 of the wire 50 forms the second region 24 of the stent 20 and the second section 54 of the wire 50 forms the first region 22 of the stent 20. In some embodiments, the second sections 54 of the wires 50 form the anchoring portion 400 of the endoluminal device 10.

As shown in FIG. 5, the wire 50 has two first sections 52 and one second section 54. However, it is within the scope of the invention for the wire 50 to have only one first section 52 and only one second section 54. In some embodiments, the length of the second section 52 of the wire 50 corresponds to the length of the anchoring portion 400 of the endoluminal device 10. In other embodiments, the position of the second section 54 of the wire 50 relative to a first end of the wire 50 corresponds to a predetermined position of the first region 22 along the length of the stent 20 after a plurality of wires 50 have been interwoven to form the first region 22 of the stent 20.

In at least one embodiment, the stent 20 has a first region and a second region and comprises a plurality of interconnected struts (not shown). In some embodiments, the struts in the first region have a greater radial force than the struts of the second region of the stent. In at least one embodiment, the struts of the first region are wider, thicker, or combinations thereof than the struts of the second region.

In at least one embodiment, the stent 20 has a first stent portion 26 and a second stent portion 28 where the first and second stent portions 26, 28 are separate stent portions that overlap one another in a region of overlap 29 to form the stent 20. One stent portion 26 forms the first end 21a of the stent 20 and the other stent portion 28 forms the second end 21b of the stent 20. Thus, the longitudinal length of each stent portion 26, 28 ($L_1, L_2$) is less than the longitudinal length of the stent 20 ($L_3$). A stent 20 having first and second stent portions 26, 28 is shown schematically in an expanded state in FIG. 7. In some embodiments, the first and second stent portions 26, 28 are delivered to the body lumen sequentially. It is within the scope of the invention for the first and second stent portions 26, 28 to be delivered sequentially on the same delivery catheter or different delivery catheters.

In some embodiments, the sleeve portion 300 has at least one sleeve 30. In one embodiment, the sleeve 30 is attached to and extends from the anchor 40. In other embodiments, the sleeve portion 300 has at least one sleeve 30 and a stent 20. The sleeve 30 has a minimum longitudinal length equal to the longitudinal length of the sleeve portion 300 and a maximum longitudinal length equal to the longitudinal length of the endoluminal device 10. In at least one embodiment, the sleeve 30 is attached to and extends from the stent 20. In one embodiment, the stent 20 has a shorter longitudinal length than the sleeve 30. In some embodiments, the anchor 40 is disposed within the stent 20.

In at least one embodiment, the sleeve 30 is an elastic or conforming polymeric covering. The sleeve 30 can be made of a material that is impermeable, semi-permeable, selectively permeable, permeable, and any combination thereof. Materials that can be used to make the sleeve 30, or sleeve composition, include but are not limited to, silicone, polystyrene-polyisobutylene-polystyrene triblock copolymer (SIBS), polyurethane, polyethylene terephthalate (PET), expanded polytetrafluoroethylene (ePTFE), and any combination thereof. In at least one embodiment, the endoluminal device 10 has a first sleeve and a second sleeve. In some embodiments, the first and second sleeves have similar properties. For example, in one embodiment both the first and the second sleeves are made from an impermeable material. In other embodiments, the first and second sleeves have different properties.

Figure 8:
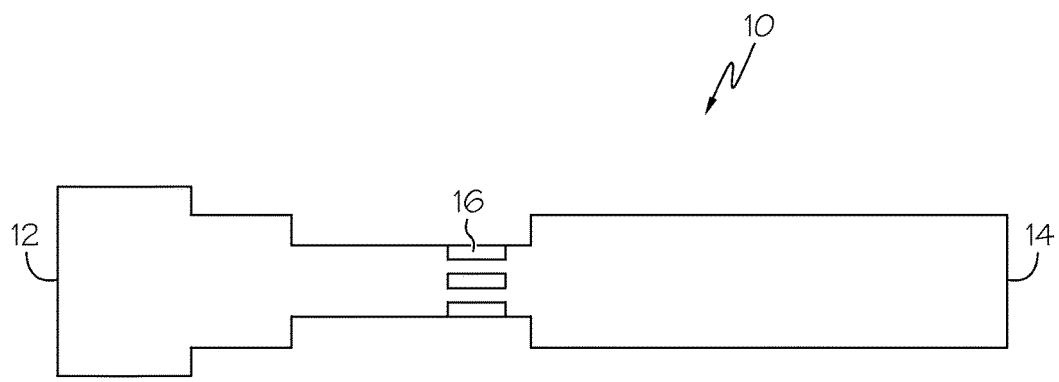
FIG. 8 is a schematic view of the endoluminal device of FIG. 2 in an expanded, deployed state.

In at least one embodiment, the endoluminal device 10 has at least one opening 16 about the circumference of the endoluminal device 10. FIG. 8 shows an endoluminal device 10 with a plurality of openings 16. The opening 16 extends from the inner surface of the endoluminal device 10 to the outer surface of the endoluminal device 10. Because the opening 16 is an opening in the wall of the endoluminal device 10, the opening(s) 16 extend through the stent 20, through the sleeve(s) 30, and any combination thereof. In some embodiments, the opening 16 is partially defined by structural members of the stent 20 and by sleeve material. In other embodiments, the opening is partially defined by structural members of the stent 20, by structural members of the anchor 40, and by sleeve material. In at least one embodiment, the first and second stent portions 26, 28 are configured to form at least one opening 16 in the region of overlap 29 (not shown).

In at least one embodiment, the opening(s) in the sleeve(s) is made by a laser. The opening(s) in the sleeve(s) can also be made by cutting, piercing, punching, or any other suitable method. In some embodiments, the opening 16 in the sleeve(s) 30 has the same shape as the opening 25 defined by the structural members of the stent 20.

In at least one embodiment, the opening(s) 16 provide a passageway for bile to move into the lumen defined by the endoluminal device 10. In some embodiments, the opening(s) 16 are positioned on the portion of the endoluminal device 10 that will be located adjacent to, or downstream from, the bile duct when the endoluminal device 10 is deployed in the gastrointestinal tract.

In at least one embodiment, the endoluminal device 10 has a variable diameter along the length of the endoluminal device 10, about the circumference of the endoluminal device 10, and any combination thereof. In some embodiments, the endoluminal device 10 has a variable diameter when it is an expanded state. In one embodiment, the variable diameter anchors the endoluminal device in a body lumen, facilitates the flow of bile, prevents the occlusion of the bile duct, prevents migration of the endoluminal device 10, conforms to the anatomy of the body lumen, and combinations thereof. A schematic view of an endoluminal device 10 with a variable diameter in an expanded state is shown in FIG. 8. Although the endoluminal device 10 shown in FIG. 8 has four sections (not labeled), that each section have a different diameter than the section(s) immediately adjacent thereto, the endoluminal device 10 can have two, three, four, five, six or more sections with different diameters than the section(s) immediately adjacent thereto.

Figure 9:
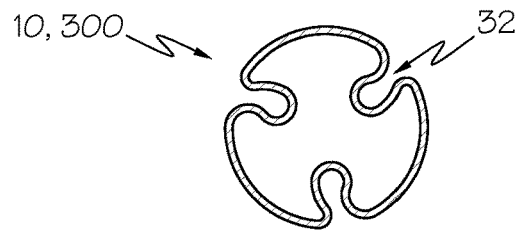
FIG. 9 is a cross-sectional view of a sleeve portion of the endoluminal device of FIG. 2.
Figure 10:
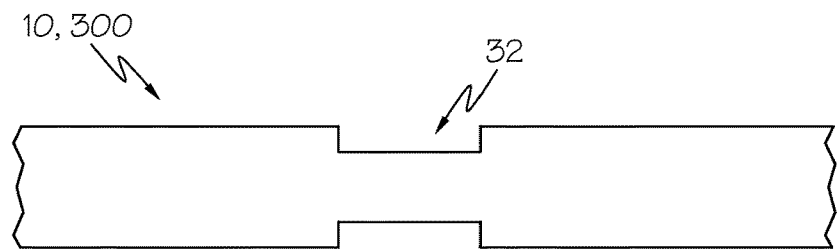
FIG. 10 is a schematic view of a sleeve portion of the endoluminal device of FIG. 2.

In some embodiments, the sleeve portion 300 has a variable diameter about the circumference. In one embodiment, the sleeve portion 300 has at least one groove 32 thereby providing the sleeve portion 300 with a variable circumferential diameter. An example of a sleeve portion 300 with grooves 32 is shown in FIG. 9. It is within the scope of the invention for the sleeve portion 300 to have one, two, three, four, five, six, seven, eight, nine, ten or more grooves 32. In some embodiments, the grooves 32 are parallel to a longitudinal axis of the endoluminal device 10. In other embodiments, the grooves 32 are arranged spirally about the sleeve portion 300. In one embodiment, the each groove 32 extends along the entire length of the sleeve portion 300. In other embodiments, the sleeve portion 300 has a variable diameter along the length of the sleeve portion 300. As shown in for example in FIG. 10, the sleeve portion 300 has grooves 32 which extend about the circumference of the endoluminal device 10.

In at least one embodiment, the endoluminal device 10 has at least one engagement mechanism 60. In some embodiments, the engagement mechanism 60 engages the endolumenal device 10 to the body lumen, prevents migration of the endoluminal device 10, engages the stent 20 to the sleeve 30, engages the anchor 40 to the stent 20 and the sleeve 30, and combinations thereof. Engagement mechanisms 60 include for example, variable diameter of the endoluminal device 10; the anchor 40; barbs 62; the shape 64 of the anchoring portion 400; and combinations thereof.

Figure 11:
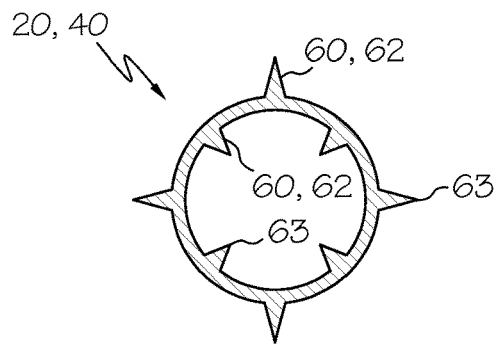
FIG. 11 is a cross-sectional view of a portion of the endoluminal device of FIG. 2 having a plurality of barbs.
Figure 12:
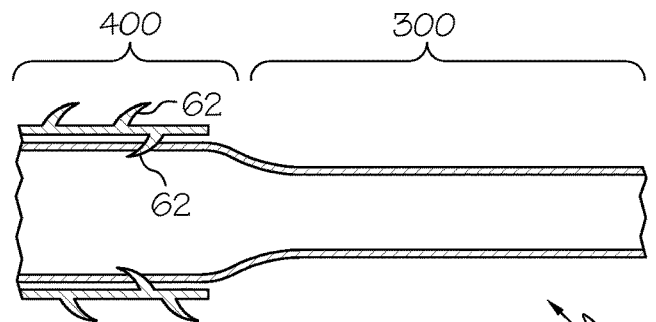
FIG. 12 is a cross-sectional view of an embodiment of the endoluminal device of FIG. 2.

In at least one embodiment, the anchoring portion 400 has a plurality of barbs 62. In some embodiments, the anchor 40 has a plurality of barbs 62. In other embodiments, only the proximal region of the stent 20 has a plurality of barbs 62. For simplicity, the discussion regarding barbs 62 will refer to stent 20. However, the same discussion also applies to an anchor 40 that has a plurality of barbs 62. It is within the scope of the invention for the barbs 62 to be integral to the stent 20, or for the barbs 62 to be attached to the stent 20, and any combination thereof. In some embodiments, the barbs 62 are sharp bends in the wires 50 interwoven to form the anchor 40 or the proximal region of stent 20. The plurality of barbs 62 may be located on the inner surface of the stent 20, the outer surface of the stent 20, and any combination thereof. FIG. 11 shows a stent 20, that has a plurality of barbs 62 on both the inner surface and the outer surface. Each barb 62 extends away from the surface of the stent 20. In some embodiments, the tip 63 of each barb 62 is parallel to the longitudinal axis of the endoluminal device 10. As shown in FIG. 12, the barbs 62 on the inner surface of the stent 20 and the barbs 62 on the outer surface of the stent 20 face in opposite directions (note that the tips of the barbs 62 face in opposite directions).

FIG. 12 shows an endoluminal device with an anchoring portion 400 that has a plurality of barbs 62. As discussed above, in some embodiments, the anchoring portion 400 may be a separate anchor 40 and in other embodiments, a portion of the stent 20 forms the anchoring portion. As shown in FIG. 12, the plurality of barbs 62 on the inner surface of the stent 20 engages the stent 20 and the sleeve 30 to one another. The plurality of barbs 62 on the outer surface of the stent 20 engages the endoluminal device 10 to the body lumen. In some embodiments, the barbs 62 of the stent 20 reversibly engage the stent 20 and the endoluminal device 10 to one another, as discussed below in greater detail. In one embodiment, the endoluminal device 10 has only a sleeve 30 to which the anchor 40 is reversibly engaged.

In at least one embodiment, the anchor 40 has a plurality of barbs 62. In some embodiments, the anchor 40 is reversibly engaged to a stent-sleeve 20,30. A stent-sleeve 20-30 is a stent 20 and sleeve 30 that have been engaged to one another before implantation into a body lumen, as discussed below in greater detail.

Figure 13:
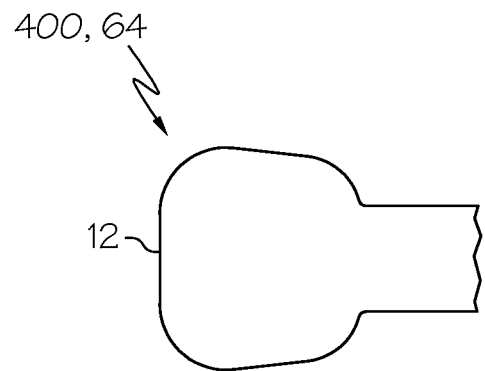
FIG. 13 is a view of an anchoring portion of the endoluminal device of FIG. 2.
Figure 14:
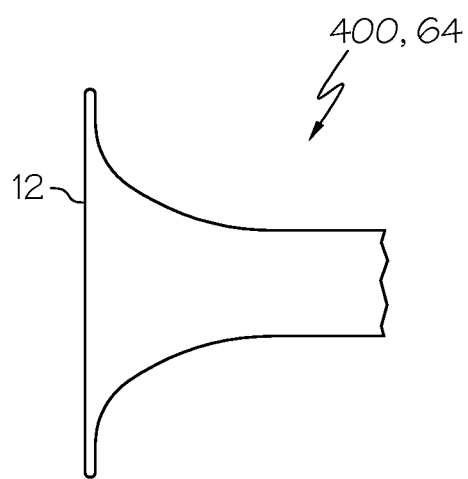
FIG. 14 is a view of an anchoring portion of the endoluminal device of FIG. 2.

In other embodiments, the shape 64 of the anchoring portion 400 is complementary to the shape of the portion of the body lumen at which the anchoring portion 400 of the endoluminal device 10 is to be positioned. In this embodiment, the shape 64 of the anchoring portion 400 engages the endoluminal device 10 to the body lumen, prevents migration of the endoluminal device 10, and combinations thereof. An anchoring portion 400 that is to be located at the duodenal bulb has a shape 64 complementary to the shape of the duodenal bulb, as shown for example in FIG. 13. FIG. 14 shows an example of the shape 64 of an anchoring portion 400 that is to be positioned at the antrum region of the stomach 102. In some embodiments, at least a portion of the anchoring portion 400 has a variable diameter, as shown for example in FIGS. 13 and 14. In other embodiments, at least a portion of the anchoring portion 400 has a diameter greater than the diameter of the distal end region of the endoluminal device 10. As discussed above, in some embodiments the anchoring portion 400 is a separate anchor 40. In those embodiments, the anchor 40 has a variable diameter. In other embodiments, a portion of the stent 20 forms the anchoring portion 400. In those embodiments, the portion of the stent 20 forming the anchoring portion 400 has a variable diameter.

In at least one embodiment, the endoluminal device 10 has at least one radiopaque marker. In some embodiments, the anchoring region 400 has at least one radiopaque marker. In other embodiments, at least some of the wires 50 forming the stent 20 of the endoluminal device include at least a portion made of radiopaque material. In one embodiment, the radiopaque material forms the core of the wire(s). Wires having a core of radiopaque material, methods of making wires with a core of radiopaque material, and expandable devices made with wires that have a core of radiopaque material are discussed in U.S. Pat. Nos. 5,679,470, 5,824,077, 6,527,802, 7,101,392, the entire contents of each are incorporated herein by reference. In one embodiment, the radiopaque marker(s) aid in positioning the endoluminal device 10 at the desired location in the body lumen.

In at least one embodiment, a sleeve 30 is attached to the stent 20 discussed above after the stent 20 has been formed and before the endoluminal device 10 is deployed in a body lumen, a stent-sleeve 20-30. In some embodiments, the sleeve 30 is disposed on the outer surface of the stent 20. In one embodiment, the sleeve 30 is formed by dipping the stent 20 into a sleeve composition. Briefly, the stent 20 is mounted onto a coating mandrel and the assembly is dipped into a polymeric solution. Then the solvent of the polymeric solution is evaporated and the polymer is cured. In another embodiment, the sleeve 30 is formed by spraying the sleeve composition onto the stent 20. Briefly, the stent is mounted onto a coating mandrel and the assembly is sprayed with a polymeric solution. Then the solvent of the polymeric solution is evaporated and the polymer cured. As discussed above, the sleeve composition is an elastic covering so that the sleeve 30 expands with the stent 20 as the endoluminal device 10 is deployed in a body lumen.

In at least one embodiment, the stent 20 and the sleeve 30 are mounted onto a mandrel and a covering material is applied to the stent 20 and the sleeve 30 thereby engaging the stent 20 and sleeve 30 together. Suitable materials for the covering material include silicone, polystyrene-polyisobutylene-polystyrene triblock copolymer (SIBS), polyurethane, and any combination thereof. In some embodiments, the sleeve 30 is a preformed tube. In other embodiments, the sleeve 30 is a sheet of material that is formed into a tube, placed onto the mandrel and the covering material is applied to engage the edges of the sheet of sleeve material together to form a tubular sleeve 30 and the covering material is applied to engage the sleeve 30 to the stent 20. In some embodiments, the covering material is applied to the entire length of the endoluminal device 10. In other embodiments, the covering material is applied only to a portion of the endoluminal device 10 to engage the stent 20 and the sleeve 30 together. In at least one embodiment, the sleeve(s) 30 is an ePTFE layer attached to the stent 20. In one embodiment, the ePTFE layer is attached to the stent 20 by an elastomer such as silicone for example. In another embodiment, the sleeve(s) 30 is attached to the stent 20 by gluing, by welding, by a fastening device, and combinations thereof.

In at least one embodiment, the sleeve 30 has a plurality of holes 34 and at least one wire 50 is woven through the holes 34 and with one another to form the endoluminal device 10. In this embodiment, portions of each wire 50 woven through the holes are positioned on an inner surface of the sleeve 30 and other portions of each wire 50 are positioned on the outer surface of the sleeve 30. In one embodiment, the wires 50 are formed of a stent material. Each hole 34 has a size sufficient for a wire to be inserted therethrough. A schematic drawing of a sleeve 30 with a plurality of holes 34 is shown for example in FIG. 15 and a schematic drawing of at least one wire 50 interwoven in a portion of the holes 34 of the sleeve is shown for example in FIG. 16.

Figure 15:
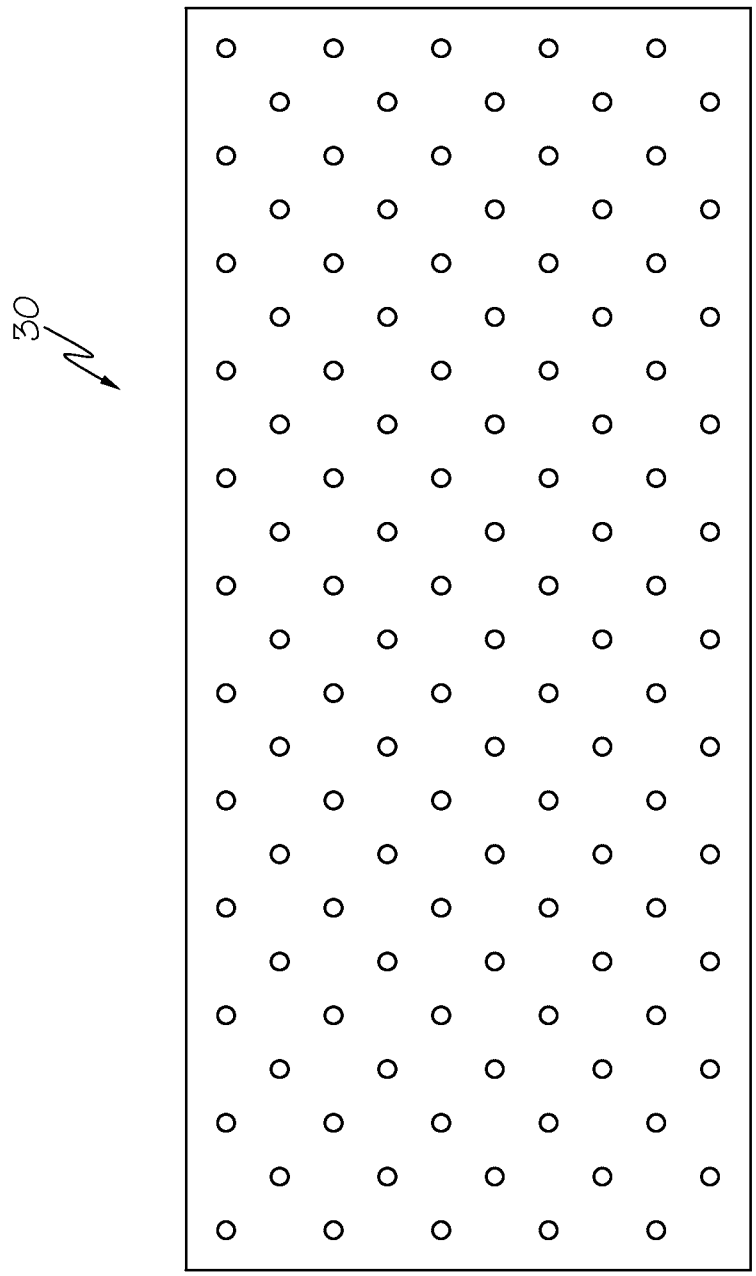
FIG. 15 is a schematic of a sleeve with a plurality of holes.
Figure 16:
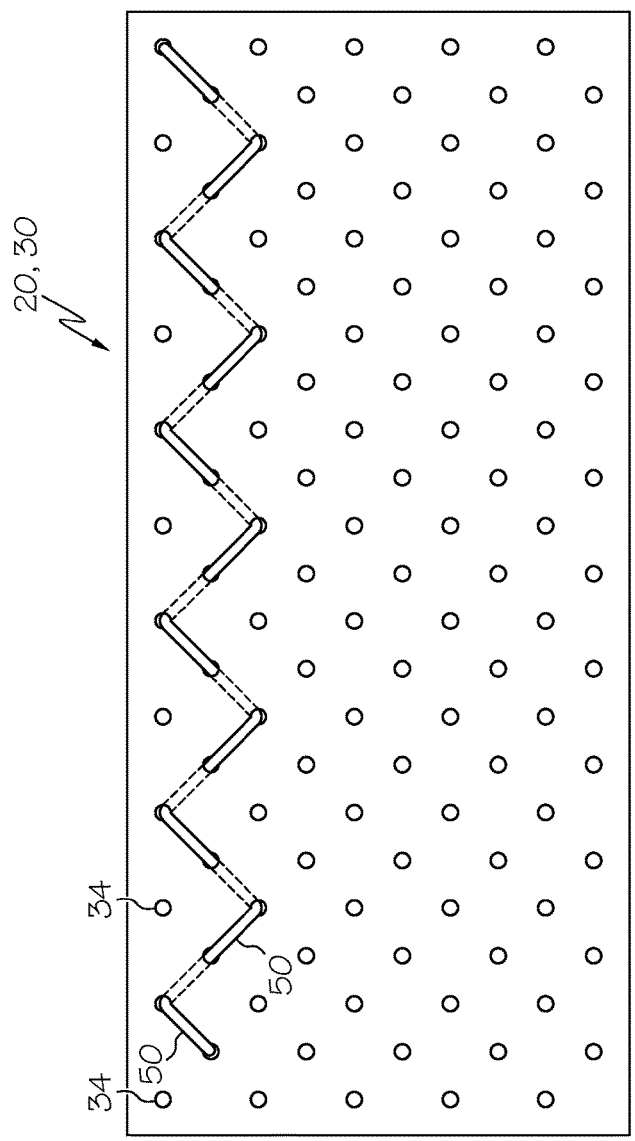
FIG. 16 is a view of the sleeve of FIG. 15 with a wire interwoven through a portion of the holes.

In some embodiments, the plurality of holes 34 extends along the entire longitudinal length of the sleeve 30, as shown in FIG. 15. It is within the scope of the invention for the plurality of holes 34 to have the same density along the length of the sleeve 30 or for the density of the holes to vary along the length of the sleeve 30. In one embodiment, the sleeve has a first section comprising a plurality of holes at a first density and a second section comprising a plurality of holes at a second density less than the first density. In other embodiments, only a portion of the longitudinal length of the sleeve 30 has a plurality of holes 34. In one embodiment, only the proximal end region of the sleeve 30 has a plurality of holes 34 and wires 50 formed of a stent material are woven through the holes 34. In this embodiment, the longitudinal length of the stent portion 20 formed by the wires 50 is less than the longitudinal length of the sleeve 30.

In some embodiments, the plurality of wires interwoven through the plurality of holes in the sleeve comprise a group of first wires with a first radial force and a group of second wires with a second radial force less than the first radial force. In one embodiment the group of first wires are interwoven with the plurality of holes in a proximal end region of the sleeve and the group of second wires are interwoven the plurality of holes in a distal end region of the sleeve. In this embodiment, the proximal end region of the device has a first radial force and the distal end region has a second radial force where the first radial force is greater than the second radial force.

In other embodiments, the plurality of wires interwoven through the plurality of holes in the sleeve each have a first section with a first diameter and a second section with a second diameter less than the first diameter. In this embodiment, the first sections of each wire is interwoven through the holes of the proximal end region of the sleeve and the second sections of each wire are interwoven through the holes of the distal end region of the sleeve. Wires with first and second sections of different diameters are discussed above.

In at least one embodiment, at least a portion of a surface of the endoluminal device has a coating. It is within the scope of the invention for the inner surface, the outer surface, and combinations thereof to have a coating. In some embodiments, the coating provides the endoluminal device with an inner surface that promotes the movement of digested material along the endoluminal device. Coatings that promote movement of digested material include silicone. In other embodiments, the coating provides the endoluminal device with an outer surface that reduces migration of the stent thereby anchoring the endoluminal device within the body lumen.

In some embodiments the coating is applied to the outer surface of the endoluminal device by placing the endoluminal device over a mandrel and applying a coating to the endoluminal device. It is within the scope of the invention for the mandrel to be a rigid mandrel or an inflatable mandrel. In one embodiment, the coating is applied to the outer surface of the endoluminal device after the mandrel, and the endoluminal device positioned thereon, is expanded.

In at least one embodiment, the endoluminal device 10, or portions thereof, is delivered to the body lumen by at least one delivery device 70. It is within the scope of the invention for any suitable delivery device to be used to deliver the endoluminal device 10, or portions thereof, as discussed below in greater detail. Some delivery devices that can be used include a crochet type delivery device, a delivery device with a double outer tube, and a delivery device with an inner tube and an outer tube. A crochet type delivery device that can be used to deliver the endoluminal device includes the Ultraflex delivery device made by Boston Scientific Scimed, Inc. A delivery device with a double outer tube is described for example in U.S. Pat. No. 5,919,204, the entire content of which is incorporated herein by reference. In at least one embodiment, the delivery device further includes a compression sleeve or containment band (not shown). The compression sleeve or containment band extends over the stent 20, or the anchor 40, and maintains the stent 20, or the anchor 40, of the endoluminal device 10 in a reduced diameter configuration on the delivery device.

Figure 17:
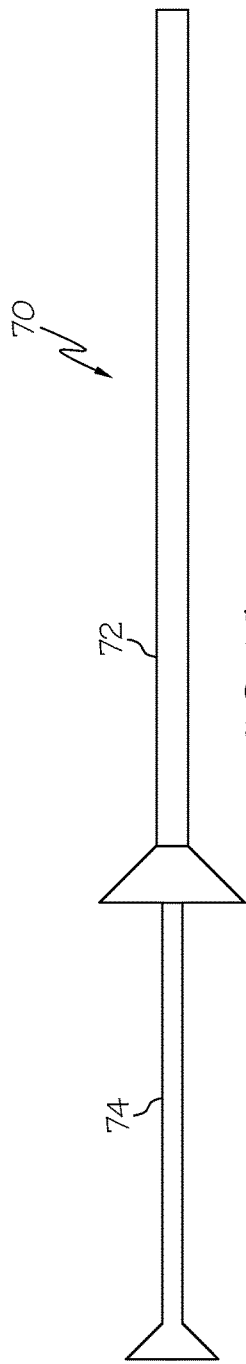
FIG. 17 is a schematic of a delivery device for the endoluminal device of FIG. 2.

A delivery device 70 with an outer tube 72 and an inner tube 74 is shown for example by the schematic drawing provided in FIG. 17. The outer tube 72 has a longitudinal length of about 110 cm to about 130 cm. In some embodiments, the endoluminal device 10, or portions thereof, is deployed when the outer tube 72 is retracted away from the endoluminal device 10. In this embodiment, the anchor 40, the stent 20, the sleeve 30, are disposed about the inner tube 74. In embodiments where the sleeve is attached to the stent before implantation of the endoluminal device 10, the stent-sleeve 20-30 is delivered together. In these embodiments, the stent-sleeve 20-30 is disposed about the inner tube 74.

As discussed above, in some embodiments the anchor 40 and the stent-sleeve 20-30 are reversibly engaged one to another by barbs 62. In this embodiment, the stent-sleeve 20-30 can be replaced with another stent-sleeve 20-30, if needed. As discussed above, in other embodiments, the stent 20 and the sleeve 30 are reversibly engaged one to another by barbs 62. In these embodiments, the sleeve 30 can be replaced with another sleeve 30. Note that the stent 20 is disposed around the sleeve 30 and that the barbs 62 maintain the position of the sleeve 30 to the stent 20 until the sleeve 30 is removed from the barbs 62 of the stent 20. To remove the sleeve 30 from the barbs of the stent 20, the sleeve is moved beyond the tip of the barbs 62.

In at least one embodiment, the portions of the endoluminal device 10 are sequentially deployed in the body lumen. In some embodiments, the portions of the endoluminal device are delivered sequentially on the same delivery device. In one embodiment, a delivery device is configured to sequentially deliver the stent 20 and the sleeve 30. In another embodiment, the delivery device is configured to sequentially deliver the anchor 40, the stent 20, and the sleeve 30. In other embodiments, the portions of the endoluminal device 10 are delivered sequentially on different delivery devices.

In at least one embodiment, the anchor 40 is deployed before the endoluminal device 10, comprising a stent 20 and a sleeve 30, is deployed. In one embodiment, the sequential deployment of the anchor 40 and the endoluminal device 10, comprising the stent 20 and the sleeve 30, is separated by a period of time so that some tissue ingrowth into the anchor 40 has occurred before the endoluminal device 10 is deployed. In one embodiment, the tissue ingrowth prevents migration of the anchor 40. Some alternative means to secure the anchor 40 to the body lumen before the sleeve 30 is attached thereto include sutures, clips, T-connectors, and any combination thereof. U.S. Pat. Nos. 6,740,121 and 6,755,869, the entire contents of which are incorporated herein by reference, describe securing a stent to a body lumen.

In at least one embodiment, the stent-sleeve 20-30 is deployed before an anchor 40 is deployed. In one embodiment, the anchor 40 has barbs 64 on the outer surface. When the anchor 40 is expanded, the barbs 64 engage the anchor 40 to the endoluminal device 10 and also to the body lumen. In at least one embodiment, the stent-sleeve 20-30 is disposed around the anchor 40 when the endoluminal device 10 is deployed in a body lumen. In some embodiments, when the endoluminal device 10 is deployed in a body lumen, a first sleeve 30 is disposed around the stent 20 which is disposed around a second sleeve 30 which is disposed around an anchor 40. In other embodiments, when the endoluminal device 10 is deployed in a body lumen, a first sleeve is disposed around the stent 20, which is disposed around the anchor 20. In still other embodiments, when the endoluminal device 10 is deployed in a body lumen, a stent 20 is disposed around a sleeve 30, which is disposed around an anchor 40.

In other embodiments, the sleeve 30 is deployed before the stent 20. In one embodiment, the stent 20 has barbs 64 on the outer surface. When the stent 20 is expanded, the barbs 64 engage the stent 20 to the sleeve 30 and also to the body lumen. In this embodiment, the sleeve 30 is disposed around the stent 20 when the endoluminal device 10 is deployed in a body lumen.

In at some embodiments, a portion of the endoluminal device 10 is positioned within the duodenum 104 and another portion of the endoluminal device 10 is positioned within the jejunum 106. In other embodiments, a portion of the endoluminal device 10 is positioned above the gastroesophageal junction. In this embodiment, the endoluminal device 10 extends through the stomach 102, the duodenum 104, and a part of the jejunum 106. In at least one embodiment, an endoluminal device 10 that has a portion extending through the stomach 102 is resistant to the acidic environment of the stomach. In some embodiments, at least a portion of the endoluminal device 10 is made of an acid resistant material. In one embodiment, at least a portion of the endoluminal device 10 has a coating of an acid resistant material. Non-limiting examples of materials that are resistant to acidic environments (acid resistant materials) include silicone, polystyrene-polyisobutylene-polystyrene triblock copolymer (SIBS), and combinations thereof. In at least one embodiment, the endoluminal device 10 is positioned within the gastrointestinal tract so that the proximal end of the endoluminal device 10 is placed just distal to the papilla of Vaters, i.e. just below the bile duct.

In at least one embodiment, the endoluminal device 10 is used to treat obesity, complications of obesity, and combinations thereof. In some embodiments, the endoluminal device 10 when implanted in a body lumen results in weight reduction. In at least one embodiment, the endoluminal device 10 is implanted into a portion of the gastrointestinal tract. In some embodiments, the endoluminal device 10 is removed after a predetermined amount of weight has been lost by the patient.

The stents 20 and anchor(s) 40 of the endoluminal device 10 may be made from any suitable biocompatible materials including one or more polymers, one or more metals or combinations of polymer(s) and metal(s). Polymers that may be used include polyester and polycarbonate copolymers. Examples of suitable metals include, but are not limited to, titanium, tantalum, platinum, tungsten, gold and alloys of any of the above-mentioned metals. Examples of suitable alloys include stainless steel, platinum-iridium alloys, cobalt-chromium alloys including Elgiloy and Phynox, MP35N alloy and nickel-titanium alloys, for example, Nitinol.

The stents 20 and anchor(s) 40 of the endoluminal device 10 may be made of shape memory materials, such as superelastic Nitinol, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

In some embodiments the stent, the delivery system or other portion of the endoluminal device 10 may include one or more areas, bands, coatings, members, etc. that is (are) detectable by imaging modalities such as X-Ray, MRI, ultrasound, etc. In some embodiments at least a portion of the endoluminal device 10 is at least partially radiopaque.

In some embodiments at least a portion of the endoluminal device 10 is configured to include one or more mechanisms for the delivery of a therapeutic agent. Often the agent will be in the form of a coating or other layer (or layers) of material placed on a surface region of at least a portion of the endoluminal device 10 which is adapted to be released at the site of the endoluminal device's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The following numbered statements characterize the embodiments described above:

Statement 1. An endoluminal device, the endoluminal device comprising:
    a stent, the stent having a first end and a second end, the stent comprising:
        a plurality of interwoven wires, the plurality of interwoven wires forming a first region and a second region of the stent, each of the plurality of interwoven wires having a diameter, the diameter of at least some of the wires in the first region being greater than the diameter of the wires in the second region,
a plurality of openings between the first and second ends of the stent, the plurality of openings defined by the plurality of interwoven wires; and
an expansible sleeve, the expansible sleeve attached to the stent so that it extends over at least some of the plurality of openings of the stent.

Statement 2. The endoluminal device of statement 1, wherein the first region has a first radial force and the second region has a second radial force, the second radial force being less than the first radial force.

Statement 3. The endoluminal device of statements 1-2, the first region of the stent having a first length, the second region of the stent having a second length, the first length being less than the second length.

Statement 4. The endoluminal device of statements 1-3, wherein the density of the plurality of interwoven wires in the first region is greater than the density of the plurality of wires in the second region.

Statement 5. The endoluminal device of statements 1-3, each of the plurality of interwoven wires having a length, the diameter of each of the plurality of interwoven wires being variable along the length of the wire, the variable diameter comprising a first diameter and a second diameter, the first diameter being greater than the second diameter, wherein each of the plurality of interwoven wires having a first section with a first length and a second section with a second length, the first section forming the first region of the stent and the second section forming the second region of the stent, the first section having the first diameter along the first length and the second section having the second diameter along the second length.

Statement 6. The endoluminal device of statements 1-4, each of the plurality of interwoven wires having a length, the diameter of each of the plurality of interwoven wires being substantially the same along the length of the wire, the plurality of interwoven wires comprising a plurality of first wires and a plurality of second wires, the plurality of first wires having a first diameter, the plurality of second wires having a second diameter, the first diameter greater than the second diameter, wherein the second region of the stent is formed only of the plurality of second wires.

Statement 7. The endoluminal device of statement 5, the first region of the stent being formed by the plurality of first wires and the plurality of second wires, wherein the plurality of first wires forms a first braid and the plurality of second wires are interwoven into the first braid.

Statement 8. The endoluminal device of statement 5, the first region of the stent being formed only by the plurality of first wires, and wherein the plurality of second wires is engaged to the plurality of first wires.

Statement 9. The endoluminal device of statements 6-8, the plurality of first wires being a greater number than the plurality of second wires.

Statement 10. The endoluminal device of statements 1-9, the expansible sleeve being made of an impermeable material.

Statement 11. The endoluminal device of statements 1-10, the endoluminal device having a wall, the wall comprising the stent and the expansible sleeve, the expansible sleeve comprising at least one opening, the at least one opening of the expansible sleeve being aligned with one of the plurality of openings defined by the plurality of interwoven wires so that the wall of the endoluminal device comprises at least one opening.

Statement 12. The endoluminal device of statements 1-11, the endoluminal device having a variable diameter about a circumference of the endoluminal device, a variable diameter along the length of the endoluminal device, and combinations thereof.

Statement 13. The endoluminal device of statements 1-12, the expansible sleeve having a plurality of grooves.

Statement 14. The endoluminal device of statements 1-13, wherein at least some of the plurality of interwoven wires have a core made of a radiopaque material.

Statement 15. The endoluminal device of statements 1-14, wherein the stent has a proximal end and a distal end, the sleeve extending beyond the distal end of the stent so that the stent and the sleeve form a proximal end of the endoluminal device and the sleeve forms a distal end of the endoluminal device.

Statement 16. The endoluminal device of statements 1-15, the endoluminal device having an engagement mechanism, the engagement mechanism engaging the stent to the sleeve, the endoluminal device to a body lumen, and any combination thereof.

Statement 17. The endoluminal device of statement 16, wherein the engagement mechanism is an anchoring portion, the anchoring portion having a shape when the endoluminal device is in an expanded state that is complementary to a shape of a portion of the gastrointestinal tract.

Statement 18. The endoluminal device of statement 17, wherein the at least a portion of the first region of the stent is the anchoring portion.

Statement 19. The endoluminal device of statement 17, where in the portion of the gastrointestinal tract is selected from the duodenal bulb or the antrum region of the stomach.

Statement 20. A gastrointestinal device, the gastrointestinal device having an expanded state, comprising:
a stent, the stent having a first end and a second end, the stent comprising:
a plurality of interwoven wires, the plurality of interwoven wires forming a first region and a second region of the stent, the first region having a first radial force when the stent the gastrointestinal device is in the expanded state, the second region having a second radial force when the gastrointestinal device is in the expanded state, the second radial force being less than the first radial force,
a plurality of openings between the first and second ends of the stent, the plurality of openings defined by the plurality of interwoven wires; and
a sleeve, the sleeve attached to the stent so that it extends over at least some of the plurality of the openings of the stent.

Statement 21. The gastrointestinal device of statement 20, wherein the density of the plurality of interwoven wires in the first region is greater than the density of the plurality of wires in the second region.

Statement 22. The gastrointestinal device of statement 20, wherein the plurality of interwoven wires include wires having a first diameter and wires having a second diameter, the first diameter being greater than the first diameter, wherein the first region includes wires having the first diameter and the second region consists of wires having the second diameter.

Statement 23. The gastrointestinal device of statement 20, wherein each of the plurality of interwoven wires has a first section with a first diameter and a second section with a second diameter, the first diameter being greater than the second diameter.

Statement 24. The gastrointestinal device of statement 23, wherein the first section of the plurality of interwoven wires forms the first region of the stent and the second section of the plurality of interwoven wires forms the second region of the stent.

Statement 25. A method of forming an endoluminal device comprising:

forming a stent from a plurality of wires, the plurality of wires being interwoven, the plurality of interwoven wires forming a first region and a second region of the stent, each of the plurality of interwoven wires having a diameter, the diameter of at least some of the wires in the first region being greater than the diameter of the wires in the second region, the stent further having a plurality of openings defined by the plurality of interwoven wires.

Statement 26. The method of statement 25 further comprising:

attaching a sleeve to the stent, the sleeve extending over at least some of the plurality of openings of the stent, the sleeve being made of an expansible material.

Statement 27. The method of statement 25, each of the plurality of wires having a length, the diameter of each of the plurality of wires being variable along the length of the wire, the variable diameter comprising a first diameter and a second diameter, the first diameter being greater than the second diameter, each of the plurality of interwoven wires having a first section with a first length and a second section with a second length, the first section forming the first region of the stent and the second section forming the second region of the stent, the first section having the first diameter along the first length and the second section having the second diameter along the second length.

Statement 28. The method of statement 25, each of the plurality of interwoven wires having a length, the diameter of each of the plurality of interwoven wires being substantially the same along the length of the wire, the plurality of interwoven wires comprising a plurality of first wires and a plurality of second wires, the plurality of first wires having a first diameter, the plurality of second wires having a second diameter, the first diameter greater than the second diameter, the second region of the stent being formed only of the plurality of second wires;

wherein forming the stent comprises attaching the plurality of wires forming the second region to the plurality of wires forming the first region.

Statement 29. The method of statement 26, the sleeve further comprising at least one opening, wherein attaching the sleeve to the stent further comprises aligning each opening of the sleeve with one of the openings defined by the plurality of wires.

Statement 30. A method of treating at least one complication of obesity, the method comprising:

implanting an endoluminal device in a portion of a gastrointestinal tract, the endoluminal device comprising a stent and a sleeve; the stent having a first end and a second end, the stent comprising:

a plurality of interwoven wires, the plurality of interwoven wires forming a first region and a second region of the stent, at least some of the plurality of wires forming the first region having a first diameter, and at least some of the plurality of wires forming the first region having a second diameter, the second diameter being smaller than the first diameter, and a plurality of openings between the first and second ends of the stent, the plurality of openings defined by the plurality of interwoven wires;

the sleeve being attached to the stent so that it extends over at least some of the plurality of openings of the stent.

Statement 31. The method of statement 30, the endoluminal device having a distal end region, the distal end region being positioned in a portion of the small intestine.

Statement 32. The method of statement 31, the gastrointestinal tract comprising a stomach, the stomach having an antrum region, the endoluminal device having a proximal end region, a portion of the proximal end region being positioned at the antrum region of the stomach.

Statement 33. The method of statement 31, the gastrointestinal tract comprising a duodenal bulb, the endoluminal device having a proximal end region, a portion of the proximal end region being positioned at the duodenal bulb.

Statement 34. The method of statement 30, the at least one complication being coronary artery disease, hypertension, diabetes, gallstones, nonalcoholic steatohepatitis, pulmonary hypertension, sleep apnea, and combinations thereof.

Statement 35. A method of treating at least one complication of obesity, the method comprising:

advancing a first catheter to a desired location in a gastrointestinal tract, the first catheter configured to deploy a stent with a sleeve attached thereto;

deploying the stent with the sleeve attached thereto into the gastrointestinal tract;

withdrawing the first catheter;

advancing a second catheter to the desired location in the gastrointestinal tract, the second catheter configured to deploy an anchor;

deploying the anchor so that the anchor expands within the stent with the sleeve attached thereto.

Statement 36. A method of deploying an endoluminal device, the endoluminal device comprising a sleeve and a stent, the method comprising:

deploying the sleeve at a desired location within the gastrointestinal tract; and deploying the stent at the desired location within the gastrointestinal tract, the stent having an outer surface, a portion of the outer surface comprising a plurality of barbs, the plurality of barbs extending through the sleeve and into a wall of the gastrointestinal tract thereby anchoring the stent and the sleeve to the gastrointestinal tract.

Statement 37. The method of statement 36, wherein the sleeve and the stent are sequentially deployed by the same catheter.

Statement 38. The method of statement 36, wherein the sleeve is deployed by a first catheter and the stent is deployed by a second catheter.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. An endoluminal device comprising:
a first braided stent having a first longitudinal length and extending from a first end of the endoluminal device, the first braided stent formed from a first quantity of first wires;
a second braided stent having a second longitudinal length extending from the first end to a second end of the endoluminal device, the second longitudinal length greater than the first longitudinal length, the second braided stent formed from a second quantity of second wires, wherein the first quantity of first wires is less than the second quantity of second wires, wherein all wires forming the second braided stent extend from the first end to the second end;
a polymeric sleeve having a third longitudinal length equal to the second longitudinal length, wherein the polymeric sleeve has a plurality of holes extending therethrough;
the first braided stent and the second braided stent being coaxial and at least partially concentric, the first braided stent, the second braided stent and the polymeric sleeve being engaged one to another;
the first braided stent, a first longitudinal portion of the second braided stent, and a first longitudinal portion of the polymeric sleeve forming an anchoring portion of the endoluminal device; and
a second longitudinal portion of the second braided stent and a second longitudinal portion of the polymeric sleeve forming a sleeve portion of the endoluminal device, wherein the sleeve portion is devoid of the first braided stent, wherein the second longitudinal portions of the second braided stent and the polymeric sleeve both extend away from the anchoring portion and are coextensive;
wherein the first longitudinal portion of the second braided stent is shorter than the second longitudinal portion of the second braided stent, wherein the second braided stent is interwoven with the first braided stent;
wherein the anchoring portion is cylindrical and has a constant diameter along its length that is larger than a diameter of the sleeve portion when the endoluminal device is in an expanded state; and
wherein the diameter of the sleeve portion decreases in diameter in a distal direction from the diameter of the anchoring portion to a smaller diameter at the second end of the endoluminal device;
wherein at least some of the first quantity of first wires forming the first braided stent are woven through the plurality of holes in only a proximal end of the polymeric sleeve such that first portions of at least some first wires are positioned on an inner surface of the polymeric sleeve and second portions of at least some first wires are positioned on an outer surface of the polymeric sleeve; and
wherein at least some of the second quantity of second wires forming the second braided stent are woven through the plurality of holes in only a distal end of the polymeric sleeve such that first portions of at least some second wires are positioned on an inner surface of the polymeric sleeve and second portions of at least some second wires are positioned on an outer surface of the polymeric sleeve.

2. The endoluminal device of claim 1, wherein the anchoring portion has a length of 2 cm to 6 cm and the sleeve portion has a longitudinal length of 24 cm to 88 cm.

3. The endoluminal device of claim 1, wherein the first longitudinal portion of the second braided stent has a greater radial force than the second longitudinal portion of the second braided stent.

4. The endoluminal device of claim 1, wherein the anchoring portion has a greater radial force than the sleeve portion.

5. The endoluminal device of claim 1, wherein the polymeric sleeve is impermeable.

6. The endoluminal device of claim 1, wherein the first wires have a first diameter and the second wires have a second diameter that is less than the first diameter.

7. The endoluminal device of claim 1, further comprising one or more openings extending through the polymeric sleeve in a middle portion of the endoluminal device, the one or more openings in fluid communication with a lumen of the endoluminal device.

8. An endoluminal device comprising:
first and second coaxial stents and a polymeric sleeve engaged to one another, the first coaxial stent being formed by a first plurality of interwoven wires and the second coaxial stent being formed by a second plurality of interwoven wires, the first and second coaxial stents having different longitudinal lengths and being at least partially concentric, the polymeric sleeve having a longitudinal length and a plurality of holes extending therethrough;
an anchoring portion forming a first end of the endoluminal device, the anchoring portion including the first and second coaxial stents and a proximal end of the polymeric sleeve; and
a sleeve portion forming a second end of the endoluminal device, the sleeve portion including the polymeric sleeve and only the second coaxial stent, wherein all wires forming the second coaxial stent extend from the first end of the endoluminal device to the second end of the endoluminal device, wherein the polymeric sleeve and the second coaxial stent is coextensive along the entire longitudinal length of the polymeric sleeve, wherein the sleeve portion is longer than the anchoring portion;
wherein the first coaxial stent is interwoven with the second coaxial stent;
wherein at least some of the first plurality of interwoven wires forming the first coaxial stent are woven through the plurality of holes in only a proximal end of the polymeric sleeve such that first portions of at least some of the first plurality of interwoven wires are positioned on an inner surface of the polymeric sleeve and second portions of at least some of the first plurality of interwoven wires are positioned on an outer surface of the polymeric sleeve; and
wherein at least some of the second plurality of interwoven wires forming the second coaxial stent are woven through the plurality of holes in only a distal end of the polymeric sleeve such that first portions of at least some of the second plurality of interwoven wires are positioned on an inner surface of the polymeric sleeve and second portions of at least some of the second plurality of interwoven wires are positioned on an outer surface of the polymeric sleeve.

9. The endoluminal device of claim 8, wherein a radial force of the anchoring portion is 10 to 1,000 times greater than a radial force of the sleeve portion.

10. The endoluminal device of claim 8, wherein the polymeric sleeve comprises silicone and the plurality of holes has a density that varies along the longitudinal length of the polymeric sleeve.

11. The endoluminal device of claim 8, wherein the longitudinal length of the polymeric sleeve is equal to a longitudinal length of the endoluminal device, the anchoring portion further including the polymeric sleeve.

12. The endoluminal device of claim 8, wherein the anchoring portion comprises a plurality of barbs.

13. The endoluminal device of claim 8, wherein the plurality of holes extends along only a portion of the longitudinal length of the polymeric sleeve.

14. The endoluminal device of claim 8, wherein the interwoven wires in the anchoring portion have a first diameter and the interwoven wires in the sleeve portion have a second diameter that is less than the first diameter.

15. An endoluminal device comprising a wall formed by:
a first braided stent having a first longitudinal length extending to a first end of the endoluminal device and being formed from a first quantity of wires;
a second braided stent having a second longitudinal length greater than the first longitudinal length and being formed from a second quantity of wires that is greater than the first quantity of wires, the second braided stent extending from the first end to a second end of the endoluminal device, wherein all wires forming the second braided stent extend from the first end to the second end;
a tubular silicone sleeve having a plurality of holes extending therethrough;
wherein the first braided stent, the second braided stent and the silicone sleeve are engaged one to another, the first braided stent and the second braided stent are coaxial and at least partially concentric, the first braided stent, the second braided stent, and the silicone sleeve forming an anchoring portion of the endoluminal device, and only the second braided stent and the silicone sleeve forming a sleeve portion of the endoluminal device, the sleeve portion extending from the anchoring portion, the sleeve portion being longer than the anchoring portion, wherein the second braided stent is interwoven with the first braided stent;
wherein the second braided stent extends to an end of the silicone sleeve opposite the anchoring portion;
wherein the anchoring portion comprises a plurality of barbs disposed on an outer surface of the anchoring portion, the barbs defined by sharp bends in at least some of the first and/or second quantity of wires; and
wherein the endoluminal device further comprises one or more openings positioned intermediate the first and second ends of the endoluminal device, the one or more openings extending from an inner surface of the endoluminal device to an outer surface of the endoluminal device thereby providing a passageway into a lumen defined by the endoluminal device
wherein at least some of the first quantity of first wires forming the first braided stent are woven through the plurality of holes in only a proximal end of the silicone sleeve such that first portions of at least some of the first wires are positioned on an inner surface of the silicone sleeve and second portions of at least some of the first wires are positioned on an outer surface of the polymeric sleeve; and
wherein at least some of the second quantity of second wires forming the second braided stent are woven through the plurality of holes in only a distal end of the silicone sleeve such that first portions of at least some of the second wires are positioned on an inner surface of the silicone sleeve and second portions of at least some of the second wires are positioned on an outer surface of the silicone sleeve.

16. The endoluminal device of claim 15, wherein the anchoring portion has a greater radial force than the sleeve portion.

17. The endoluminal device of claim 15, wherein the tubular silicone sleeve includes at least one groove extending spirally around the tubular silicone sleeve.

18. The endoluminal device of claim 17, wherein the at least one groove extends along an entire length of the sleeve.

19. The endoluminal device of claim 15, further comprising a plurality of barbs disposed on an inner surface of the anchoring portion, wherein the plurality of barbs on the outer surface all face a first direction and the plurality of barbs on the inner surface all face a second direction, wherein the first direction is opposite the second direction.

* * * * *